US011737962B2

(12) United States Patent
Schmid et al.

(10) Patent No.: US 11,737,962 B2
(45) Date of Patent: Aug. 29, 2023

(54) HAIR TREATMENT PASTE

(71) Applicant: KAO GERMANY GMBH, Darmstadt (DE)

(72) Inventors: Sabine Schmid, Darmstadt (DE); Melina Sulzbach, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 113 days.

(21) Appl. No.: 17/203,118

(22) Filed: Mar. 16, 2021

(65) Prior Publication Data
US 2021/0299012 A1 Sep. 30, 2021

(30) Foreign Application Priority Data

Mar. 25, 2020 (EP) .................................... 20165658

(51) Int. Cl.
| | |
|---|---|
| A61K 8/36 | (2006.01) |
| A61K 8/9794 | (2017.01) |
| A61K 8/9789 | (2017.01) |
| A61K 8/34 | (2006.01) |
| A61K 8/37 | (2006.01) |
| A61K 8/42 | (2006.01) |
| A61K 8/60 | (2006.01) |
| A61K 8/73 | (2006.01) |
| A61K 8/81 | (2006.01) |
| A61K 8/86 | (2006.01) |
| A61Q 5/06 | (2006.01) |

(52) U.S. Cl.
CPC .............. *A61K 8/361* (2013.01); *A61K 8/342* (2013.01); *A61K 8/345* (2013.01); *A61K 8/37* (2013.01); *A61K 8/42* (2013.01); *A61K 8/60* (2013.01); *A61K 8/73* (2013.01); *A61K 8/731* (2013.01); *A61K 8/8105* (2013.01); *A61K 8/8117* (2013.01); *A61K 8/86* (2013.01); *A61K 8/9789* (2017.08); *A61K 8/9794* (2017.08); *A61Q 5/06* (2013.01)

(58) Field of Classification Search
None
See application file for complete search history.

(56) References Cited

U.S. PATENT DOCUMENTS

| | | | |
|---|---|---|---|
| 2011/0150812 A1* | 6/2011 | Mecca | ...................... A61Q 5/12 424/70.19 |
| 2018/0028435 A1* | 2/2018 | Punsch | ..................... A61K 8/31 |

FOREIGN PATENT DOCUMENTS

| | | |
|---|---|---|
| CN | 106974840 A | 7/2017 |
| EP | 2042154 A1 | 4/2009 |

OTHER PUBLICATIONS

Science-y Hair Blog "Product pH List" <http://science-yhairblog.blogspot.com/2018/12/product-ph-list.html> available Dec. 24, 2018; accessed Oct. 12, 2022 (Year: 2018).*
European Search Report dated Jun. 15, 2020, in connection with European Application No. 20165658.4.
Mintel, Database GNPD, "SOS Intense Soothing Mist", retrieved from www.gnpd.com, Feb. 28, 2018.

* cited by examiner

*Primary Examiner* — Nicole P Babson
(74) *Attorney, Agent, or Firm* — Norris McLaughlin, P.A.

(57) ABSTRACT

The present invention is on a hair treatment paste composition providing improved hair styling owing to its flexible consistency, which makes easy and homogeneous application onto hair possible. It is an aqueous composition comprising one or more triglyceride comprising fatty acyl chain with a C length from 8 to 16 C atoms, a non-ionic thickening polymer with a polymerization degree of less than or equal to 400 and an anionic thickening polymer.

19 Claims, No Drawings

HAIR TREATMENT PASTE

This application claims foreign priority benefits under 35 U.S.C. § 111 of European Application No. 20165658.4, filed Mar. 25, 2020, the disclosure of which is incorporated herein by reference.

The present invention is on a hair treatment paste composition providing improved hair styling owing to its flexible consistency, which allows easy and homogeneous application onto hair possible.

Pasty and fatty hair compositions have been known among the hair styling cosmetic products for some time. They provide hair certain level of setting, bundling and improved curl definition in form of three-dimensional appearance. However, the known products are often sticky which makes hair styling difficult. Consumers with curly hair often suffer from frizzy and tousled hair and, therefore, desire bundled hair with defined curls, with a smooth surface and a plastic three-dimensional (3D) shape. The existing products on the marker such as Briogeo Curl Charisma does not optimally provide these properties to the hair.

The inventors of the present invention has unexpectedly found out that an aqueous composition comprising triglycerides with a defined fatty acyl chain composition together with a non-ionic polymer with defined degree of polymerisation and an anionic thickening polymer provides hair stronger bundling, well-defined curly appearance, smooth surface and a plastic three-dimensional (3D) shape owing to its good flexibility so that homogeneous application onto hair may easily be carried out.

Thus, the first object of the present invention is an aqueous composition for keratin fibers, especially for human hair, comprising one or more triglyceride comprising fatty acyl chain with a C length of 8 to 16 C atoms, a non-ionic thickening polymer with a polymerization degree of less than or equal to 400 and an anionic thickening polymer.

The second object is a method of treating hair wherein the composition of the present invention is applied onto wet or dry hair, preferably wet hair, and the hair is not rinsed off.

The third object is a kit for hair comprising one or more products and/or hair appliances and a composition of the present invention.

The composition is in the form of paste preferably having viscosity of 150,000 mPa·s or more, preferably in the range of 175,000 to 1,000,000 mPa·s measured at 20° C. with a Brookfiled viscosimeter Spindle 96 at 10 rpm.

The composition is an aqueous composition and comprises water at a concentration of 20 to 90%, preferably 30 to 80% and more preferably 40 to 60% by weight, calculated to the total of the composition.

The composition comprises triglycerides comprising fatty acyl chain with a C length from 8 to 16 C atoms. The portion of the fatty acyl chain with 8 to 16 C atoms is in the range of 45 to 95%, preferably 55 to 95%, more preferably 65 to 95% by weight, calculated to the total fatty acyl chain content of the triglyceride.

The suitable non-limiting examples to the triglycerides are caprylic/capric triglyceride, palm seed oil, *Cocos nucifera* oil and Babassu oil (*Orbignya oleifera* seed oil). The most preferred is caprylic/capric triglyceride, and mixtures thereof.

The total concentration of one or more triglycerides as defined above varies in the range of 0.1 to 15%, preferably 1 to 12.5%, more preferably 2 to 10% by weight, calculated to the total of the composition.

The composition preferably comprises additional lipophilic compounds, such as fatty alcohol fatty acid ester according to the general structure

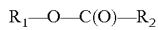

wherein $R_1$ is an straight alkyl chain with 12 to 60 C atoms and $R_2$ is a fatty acyl group with 9 to 23 C atoms, mineral oil such as paraffin oil, silicone oils such as dimethicones with various polymerization degree and, therefore, with various viscosity and volatility, and aminated silicones known with CTFA adopted name Amodimethicone available from various suppliers.

Suitable non-limiting examples are C16-36 alkyl stearate, C20-40 alkyl stearate, C30-50 alkyl stearate, C40-60 alkyl stearate and C20-40 alkyl behenate. Preferred is C16-36 alkyl stearate.

The total concentration of lipophilic compounds as defined above varies in the range of 1 to 40%, preferably 2.5 to 30%, more preferably 5 to 25% by weight, calculated to the total of the composition.

The composition comprises nonionic thickening polymer with a polymerization degree less than or equal to 400. Suitable non-limiting examples are microcrystalline cellulose, hydrogenated styrene butadiene copolymer and Polyether-1. The preferred is microcrystalline cellulose.

The concentration of nonionic thickening polymer with a polymerization degree less than or equal to 400 is in the range of 0.1 to 5%, preferably 0.2 to 3%, more preferably 0.25 to 2.5% by weight, calculated to the total of the composition.

The composition comprises anionic thickening polymer, which is preferably selected form the polymers forming a thixotropic gel. Suitable non-limiting examples are xanthan gum, acrylate homopolymers such as carbomer, acrylate copolymers such as copolymer of acrylic acid and methacrylic acid and acrylates crosspolymers such as copolymer of acrylic acid and methacrylic acid cross-linked with glycol dimethacrylate, and mixtures thereof. Preferred are xanthan gum and acrylic acid and methacrylic acid copolymer. The acrylate polymers are commercially available under the trade names such as Balance, Aculyn, Salcare, etc from various suppliers.

The concentration of anionic thickening polymer is in the range of 0.1 to 5%, preferably 0.2 to 4%, more preferably 0.5 to 3% by weight, calculated to the total of the composition.

The composition may further comprise one or more surfactants selected from anionic, nonionic and amphoteric ones. Preferred are non-ionic surfactants Suitable ones are sorbitan derivates such as polysorbate-20, Poylsorbate-80, polyglycerolated straight, branched, saturated or unsaturated fatty acids with 12 to 24 C atoms and with glycerolation degree in the range of 1 to 20, ethoxylated and/or propoxylated fatty alcohols with 12 to 24 C atoms and with 2 to 20 ethoxy and/or propoxy units. Suitable examples to ethoxylated fatty alcohols are laureth-20, ceteareth-20, ceteareth-30, ceteth-20, steareth-20 and isoceteth-20.

The total concentration of surfactants especially nonionic surfactants is in the range of 0.1 to 15%, preferably 0.2 to 12.5%, more preferably 0.5 to 10% by weight, calculated to the total of the composition.

The composition may comprise one or more polyol. Suitable ones are liquid at 20° C. such as (poly)ethylene glycols, liquid (poly)propylene glycols, glycerin and panthenol. Preferred is glycerin.

The total concentration of one or more polyol is in the range of 0.1 to 15%, preferably 0.2 to 12.5% and more preferably 0.25 to 7.5% by weight, calculated to the total of the composition.

The composition has a pH in the range of 4 to 8, preferably 4.5 to 7.5, and more preferably 5 to 7. Since the composition comprises an anionic polymer and especially the type acrylates, the pH is adjusted with an alkalizing agent, which may be aminomethylpropanol (AMP) or alkali hydroxide. Certainly if there is a need, the pH is adjusted to the required value or range using organic and/or inorganic acids well known in the art.

The following examples are to illustrate the invention but not to limit.

EXAMPLE 1

| Example 1 | |
|---|---|
| | % by weight |
| Caprylic/Capric triglyceride | 10.0 |
| C16-36 Alkyl stearate | 10.0 |
| Xanthan gum | 1.0 |
| Hydrogenated styrene butadiene Copolymer | 2.0 |
| Glycerin | 6.0 |
| Fragrance, preservative | q.s. |
| Citric acid/Sodium hydroxide | q.s. to pH 6.0 |
| Water | q.s. to 100 |
| Viscosity at 20° C. (Spd 96 10 rpm) = 200.000 mPas | |

The above composition was prepared by mixing all the components in water and melting the lipophilic waxy material at 80° C. which was followed by homogenizing at a share rate of 2500 rpm, afterwards the composition was cooled down to 40° C. while mixing and pH was adjusted and the remaining water and fragrance was added.

The above composition was tested in a half side comparative test against a commercially available product in June 2019 Briogeo Curl Charisma. Therefore, the hair of 10 volunteers were washed with a commercially available shampoo under the Brand Goldwell and hair is dried with a hair drier and equal amounts of the products were applied to each half side and hair was styled by hair dresser. Hair dressers were asked to evaluate the following parameters in a scale of 1 to 5, wherein 1 is bad, 2 is not good, 3 is acceptable, 4 is good and 5 is very good. The following results were obtained. The numbers represent the average of 10 tests.

| | Inventive composition | Comparative composition |
|---|---|---|
| Flexibility | 5 | 4 |
| Bundling | 5 | 3 |
| Frizz reduction | 5 | 4 |
| 3D curl appearance | 5 | 2 |

From the above results, it is beyond any doubt the composition according to the present invention performs far better than the comparative composition, which is the commercially available product as defined above.

Similar results were observed with the following compositions.

EXAMPLE 2

| Example 2 | |
|---|---|
| | % by weight |
| Cocos nucifera oil | 6.0 |
| Polysorbate 20 | 8.0 |
| Xanthan gum | 0.5 |
| Microcrystalline cellulose | 2.0 |
| Carnauba Wax | 6.0 |
| Propylene Glycol | 1.5 |
| Fragrance, preservative | q.s. |
| Citric acid/Sodium hydroxide | q.s. to pH 6.0 |
| Water | q.s. to 100 |

The above composition was prepared in the same way as described under example 1.

EXAMPLE 3

| Example 3 | |
|---|---|
| | % by weight |
| Babassu oil (Orbign oleifera Seed oil) | 4.0 |
| Laureth-23 | 9.0 |
| Acrylates copolymer | 3.0 |
| Acrylates Crosspolymer-4 | 2.0 |
| Polyether-1 | 4.0 |
| Dimethicone | 5.0 |
| Panthenol | 5.0 |
| Fragrance, preservative | q.s. |
| Citric acid/AMP | q.s. to pH 6.0 |
| Water | q.s. to 100 |

The above composition was prepared in the same way as described under example 1.

EXAMPLE 4

| Example 4 | |
|---|---|
| | % by weight |
| Palm seed oil | 4.0 |
| PEG-60 Almond Glycerides | 7.0 |
| Xanthan gum | 4.0 |
| Microcrystalline Wax/Cera Microcristallina | 6.0 |
| Hydrogenated Styrene Butadiene Copolymer | 2.0 |
| Panthenol | 1.5 |
| Fragrance, preservative | q.s. |
| Citric acid/Sodium hydroxide | q.s. to pH 6.0 |
| Water | q.s. to 100 |

The above composition was prepared in the same way as described under example 1.

The invention claimed is:

1. An aqueous composition for keratin fibers, the aqueous composition comprising:
   one or more triglycerides comprising fatty acyl chain with a C length from 8 to 16 carbon atoms;
   a non-ionic thickening polymer with a polymerization degree of less than or equal to 400;
   a thixotropic gel forming anionic polymer; and
   water present at a total concentration in a range of 68 to 90% by weight, calculated to a total weight of the aqueous composition,
   wherein the aqueous composition is the form of a paste having a viscosity of at least 150,000 mPa·s and up to 1,000,000 mPa·s, measured at 20° C. with a Brookfiled viscosimeter Spindle 96 at 10 rpm.

2. The aqueous composition according to claim 1, wherein the fatty acyl chain of the one or more triglycerides is present at a total concentration in a range of 45 to 95% by weight, calculated to a total fatty acyl chain content of the one or more triglyceride.

3. The aqueous composition according to claim 2, wherein the one or more triglycerides are present at a total concentration in a range of 0.1 to 15% by weight, calculated to the total weight of the aqueous composition.

4. The aqueous composition according to claim 3, wherein the one or more triglycerides are selected from caprylic/capric triglyceride, palm seed oil, *Cocos nucifera* oil and babassu oil (*Orbignya oleifera* seed oil), and mixtures thereof.

5. The aqueous composition according to claim 1, further comprising:
one or more additional lipophilic compounds selected from fatty alcohol fatty acid ester according to general structure

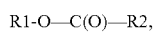
R1—O—C(O)—R2, wherein R1 is an alkyl chain with 12 to 40 carbon atoms and R2 is a fatty acyl group with 9 to 23 carbon atoms, mineral oil, silicone oils, and aminated silicones,
wherein the one or more additional lipophilic compounds are present at a total concentration in a range of 1 to 40% by weight, calculated to the total weight of the aqueous composition.

6. The aqueous composition according to claim 1, wherein the non-ionic thickening polymer is present at a total concentration in a range of 0.1 to 5% by weight, calculated to the total weight of the aqueous composition.

7. The aqueous composition according to claim 6, wherein the non-ionic thickening polymer is selected from microcrystalline cellulose, hydrogenated styrene butadiene copolymer and polyether-1, and mixtures thereof.

8. The aqueous composition according to claim 1, wherein the thixotropic gel forming anionic polymer is present at a total concentration in a range of 0.1 to 5% by weight, calculated to the total weight of the aqueous composition.

9. The aqueous composition according to claim 8, wherein the thixotropic gel forming anionic polymer is selected from xanthan gum, acrylates homopolymers, acrylates copolymers and acrylates crosspolymers, and mixtures thereof.

10. The aqueous composition according to claim 1, further comprising:
one or more surfactants selected from nonionic surfactants, anionic surfactants, and amphoteric surfactants,
wherein, when the one or more surfactants comprise nonionic surfactants, the nonionic surfactants are selected from (i) sorbitan derivates selected from polysorbate-20, polyglycerolated straight, branched, saturated or unsaturated fatty acids with 12 to 24 carbon atoms and with glycerolation degree in the range of 1 to 20, (ii) ethoxylated and/or propoxylated fatty alcohols with 12 to 24 carbon atoms and with 2 to 20 ethoxy and/or propoxy unit, and (iii) mixtures thereof, and present at a total concentration in a range of 0.1 to 15% by weight, calculated to the total weight of the aqueous composition.

11. The aqueous composition according to claim 1, further comprising:
one or more polyols that are liquid at 20° C., present at a total concentration in a range of 0.1 to 15% by weight, calculated to the total weight of the aqueous composition, and selected from liquid (poly)ethylene glycols, liquid (poly)propylene glycols, glycerin, and panthenol.

12. The aqueous composition according to claim 1, wherein the aqueous composition has a pH in the range of 4 to 8.

13. A kit for hair comprising:
one or more products and/or hair appliances; and
the aqueous composition according to claim 1.

14. The aqueous composition according to claim 1, further comprising:
water present at a total concentration in a range of 68 to 80% by weight, calculated to the total weight of the aqueous composition.

15. The aqueous composition according to claim 4, wherein the total concentration of the one or more triglycerides is in the range of 2 to 10% by weight, calculated to the total weight of the aqueous composition.

16. The aqueous composition according to claim 7, wherein the total concentration of the nonionic thickening polymer is in the range of 0.25 to 2% by weight, calculated to the total weight of the aqueous composition.

17. An aqueous composition for keratin fibers, the aqueous composition comprising:
one or more triglycerides comprising fatty acyl chain with a C length from 8 to 16 carbon atoms;
a non-ionic thickening polymer with a polymerization degree of less than or equal to 400;
a thixotropic gel forming anionic polymer;
one or more additional lipophilic compounds selected from fatty alcohol fatty acid ester according to general structure

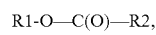
R1—O—C(O)—R2, wherein R1 is an alkyl chain with 12 to 40 carbon atoms and R2 is a fatty acyl group with 9 to 23 carbon atoms, mineral oil, silicone oils, and aminated silicones; and
water present at a total concentration in a range of 71 to 90% by weight, calculated to a total weight of the aqueous composition,
wherein the aqueous composition is the form of a paste.

18. The aqueous composition according to claim 17, wherein the total concentration of water is in the range of 71 to 80% by weight, calculated to the total weight of the aqueous composition.

19. A method of treating hair comprising:
styling hair by applying the aqueous composition according to claim 1 onto the hair, and not rinsing the aqueous composition off the hair.

* * * * *